United States Patent
Kotlyarov et al.

(10) Patent No.: US 6,683,172 B1
(45) Date of Patent: Jan. 27, 2004

(54) MAPKAP KINASE 2-INHIBITORS AND THE USE THEREOF IN ANTI-INFLAMMATORY THERAPY

(75) Inventors: Alexey Kotlyarov, Berlin (DE); Matthias Gaestel, Berlin (DE); Carola Schubert, Berlin (DE); Armin Neininger, Berlin (DE)

(73) Assignee: Max-Delbruck-Centrum fur Molekulare Medizin, Berlin (DE)

( * ) Notice: Subject to any disclaimer, the term of this patent is extended or adjusted under 35 U.S.C. 154(b) by 0 days.

(21) Appl. No.: 09/647,701
(22) PCT Filed: Apr. 1, 1999
(86) PCT No.: PCT/DE99/00990
§ 371 (c)(1), (2), (4) Date: Nov. 15, 2000
(87) PCT Pub. No.: WO99/51735
PCT Pub. Date: Oct. 14, 1999

(30) Foreign Application Priority Data

Apr. 3, 1998 (DE) .......................................... 198 14 963

(51) Int. Cl.[7] ........................ C07H 21/02; C07H 21/04; C12Q 1/68; A61K 48/00
(52) U.S. Cl. ................. 536/24.5; 536/24.3; 536/24.31; 536/24.33; 514/44; 435/6
(58) Field of Search ...................... 514/44, 2; 536/24.5, 536/24.3, 24.31, 24.33; 435/6; 530/350

(56) References Cited

PUBLICATIONS

K Miyazawa et al., Journal of Biological Chemistry, "Regulation of Interleukin–1B–induced Interleukin–6 Gene Expression in Human Fibroblast–like Synoviocytes by p38 Mitogen–activated Protein kinase,"1998, vol. 278, No. 38, pp. 24832–24838.*

Y–L Zu et al., Blood, "Activation of MAP Kinase–Activated Protein Kinase 2 in Human Neutrophils After Phorbol Ester or fMLP Peptide Stimulation," Jun. 1996, vol. 87, No. 12,pp. 5287–5296.*

AM Badger et al.,Journal of Pharmacology and Experimental Therapeutics,"Pharmacological Profile of SB 203580, ... Protein/p38 kinase, in Animal Models of Arthritis, Bone Resorption, Endotoxin Shock and Immune Function," 1996, Vol,279, No. 3, pp. 1453–1461.*

K–Y Jen et al., Stem Cells,"Suppression of Gene Expression by Targeted Disruption of Messenger RNA: Available Options and Current Strategies,"2000, 18:307–319.*

DW0 Green et al., American Colllege of Surgeons," Antisense Oligonucleotides:An Evolving Technology for the Modulation of Gene Expression in Human Disease," Jul. 2000, vol. 191, No. 1, pp. 93–105.*

AD Branch, TIBS,"A good antisense molecule is hard to find,"Feb. 1998, pp. 45–50.*

S Agrawal et al., Molecular Medicine Today, "Antisense therapetuics:is it as simple as complementary base recognition?"Feb. 2000, vol. 6, pp. 72–81.*

John C. Lee et al.; A Protein Kinase Involved in the Regulation of Inflammatory Cytokine Biosynthesis; Nature, vol. 372, Dec. 22/29, 1994; pp. 739–746.

* cited by examiner

Primary Examiner—Karen Lacourciere
(74) Attorney, Agent, or Firm—Norris McLaughlin & Marcus

(57) ABSTRACT

The invention relates to MAPKAP kinase 2 inhibitors and the use thereof in anti-inflammatory therapy. The invention can be used in the field of medicine and in the pharmaceutical industry. According to the invention, the MAPKAP kinase 2 inhibitors are used at gene level, protein level and on the basis of a specific modification of the intracellular localization of MAPKAP kinase 2. The invention makes it possible to provide targeted immune response therapy and can thus be of fundamental importance to modem medicine.

12 Claims, 1 Drawing Sheet

MAPKAP KINASE 2-INHIBITORS AND THE USE THEREOF IN ANTI-INFLAMMATORY THERAPY

BACKGROUND OF THE INVENTION

Figure 1:
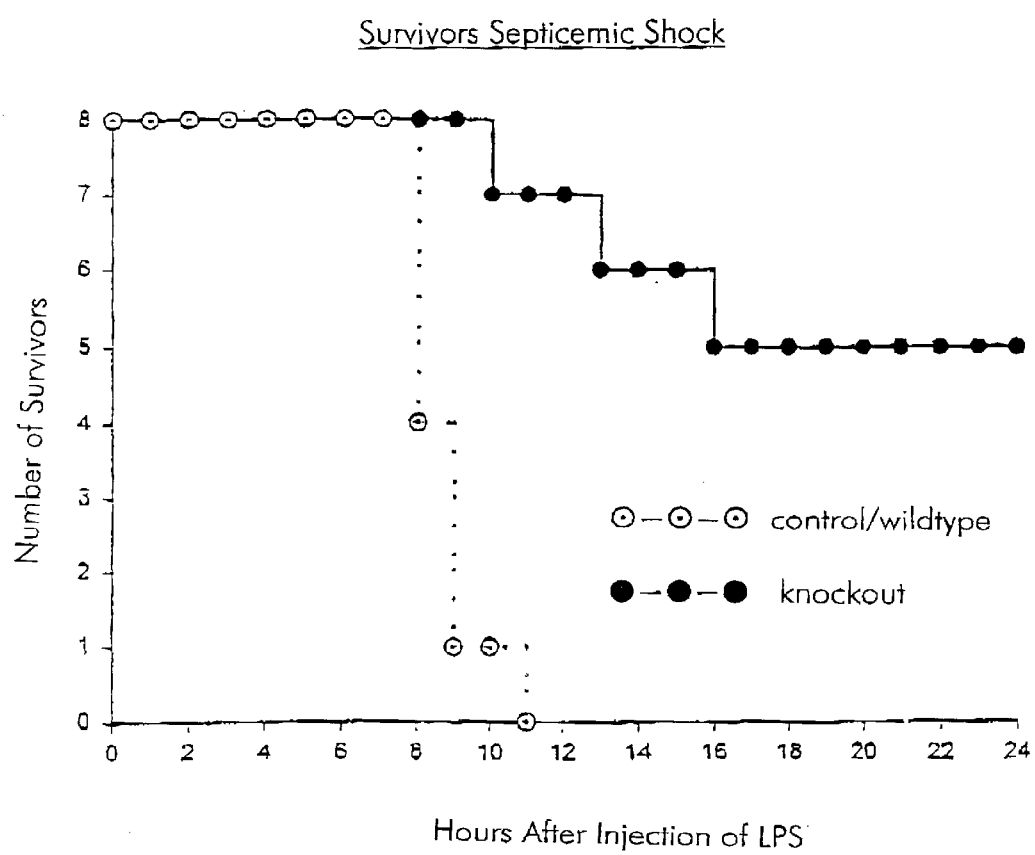

The invention relates to MAPKAP kinase 2 inhibitors and the use thereof in anti-inflammatory therapy. Fields of application of the invention are medicine and pharmaceutical industry.

A big part of all diseases is connected with inflammatory processes which result in the fact that the causes of the diseases are recognized and eliminated. The early response to an inflammation, e.g. as a reaction to bacterial lipopolysaccharides (LPS), results in the expression and release of pro-inflammatory and inflammatory cytokines and thus to massive inflammatory processes and to phenomena such as e.g. sepsis. Among the pro-inflammatory cytokines the tumor-necrosis factor α (TCFα) and interleukin-1(Il-1) stimulating, on their turn, the synthesis of further inflammatory cytokines play a central part.

Attempts have been already made to affect the course of inflammatory processes, e.g., substance S3203580 (4-(4-fluorophenyl)-2-(4-methylsulfinylphenyl-5-(4-pyridyl)-imidazole) was describe as an efficient inhibitor of cytokine biosynthesis. Its effect is based on the inhibition of protein kinase p38 MAP kinase activated by stress (also referred to as p38 reactivating kinase, P38α, p38β, CSBP-cytokine suppressive anti-inflammatory drug binding protein (J. C. Lee et al., Nature 372, 739–46 (1994)). SB203580 may as a reaction to LPS administration efficiently inhibit, at the same time, inhibiting the biosynthesis of Il-1 and TNFα. The mechanism of stimulating the cytokine biosynthesis by p38 MAP kinase has so far only been understood incompletely. Various transcription factors and protein kinases were identified a substrate of p38 MAP kinase.

These downstream components of signal transmission by p38 MAPK could individually or jointly participate in the inflammatory response.

To sum up we may state that in spite of progress having undoubtedly been made in findings a possibility to affect the process of inflammation purposefully has not yet been found.

SUMMARY OF THE INVENTION

That is why the invention is based on the task to make available a new agent based on a new principle of action which may be used as anti-inflammatory therapeutic agent with possibly small side effects.

There was found that—to our surprise—only one enzyme from the spectrum of the numerous participating enzymes plays a central part in the inflammatory response—the enzymes MAPKAP kinase 2. From this the possibility is derived to use MAPKAP kinase 2 as an ideal target for the anti-inflammatory therapy.

DRAWING

FIG. 1—chart showing survival of animals at septicaemic shock.

Survival of MAPKAP kinase 2 knock out mice at septicaemic shock caused in injection of µg LPS/20 mg galactosamine. Whereas the test animals succumb completely to the septicaemic shock after 11 h, the knock out animals show a significantly higher survival owing to a reduced inflammatory response.

DESCRIPTION OF THE PREFERRED EMBODIMENT

Accordingly the invention is marked by the specific inhibition of the effect of MAPKAP kinase 2 This may be effected in 3 various ways.

a) by antisense-oligonucleotides which are suited to specifically inhibit the expression of MAPKAP kinase 2 in human cells.

Suitable oligonucleotides are a.o.

5'-GGAGTTGGAC AGCATGGTGC CCGGGGACGC CGGGG-3'(SEQ ID No. 1)

5'-CACAGGCGGG GGTGCCCGCG GCCGCCCCCT CCTCC-3'(SEQ ID No. 2)

5'-GGGGCGGGGA ACGGCACCGG CGGGCTCTGG CCCTG-3'(SEQ ID No. 3).

b) by chemical substances suited to specifically inhibit the enzymatic activity of MAPKAP kinase 2.

Furthermore, there was found that a cell nucleus export depending on activation is required for MAPKAP kinase 2 to take effect. Thereof a further variant of the invention is derived.

c) by chemical substances suited to specifically change the intracellular localization of MAPKAP kinase 2 (translocation).

The invention permits to purposefully treat the inflammation response and may thus be of fundamental importance to modern medicine.

Hereinafter the invention shall be explained in greater detail by an example.

EXAMPLE

By means of the gene targeting method a MAPKAP K2 knock out mouse is produced. This mouse is viable showing—as far it has been examined—no pathological modification of tissue and organs, yet a clearly reduced inflammation response induced by LPS. This is shown e.g. by a significantly higher survival of the knock out mice at septiceamic shock (FIG. 1). Furthermore, 90 in after LPS stimulation in the knock outs the serum concentrations of TNFα are lower than by 10 times than the concentrations in comparable wild type animals (s. Table). These data show clearly that MAPKAP kinase 2 plays an essential part in the inflammation response, being, at the same time, not required for the normal development of the mouse.

TABLE

Serum concentration of TNFα in MAPKAP kinase 2 knock outs and wild type animals 90 min. after injection i p. of 1 µg LPS

|  | −/− (MAPKAP kinase 2 knock outs) | +/− wild type |
|---|---|---|
| TNFα (pg/ml serum) | 268 ± 156 | 4005 ± 1818 |

What is claimed is:

1. A composition for inhibiting an inflammatory response, the composition comprising,
   at least one nucleic acid molecule selected from the group consisting of SEQ ID NOS 1–3.

2. The composition of claim 1, wherein the at least one nucleic acid molecule consists of SEQ ID NO 1.

3. The composition of claim 1, wherein the at least one nucleic acid molecule consists of SEQ ID NO 2.

4. The composition of claim 1, wherein the at least one nucleic acid molecule consists of SEQ ID NO 3.

5. The composition of claim 1, wherein the inhibited inflammatory response is mediated by MAPKAP kinase 2.

6. A composition that Inhibits a mammalian cell's production of at least one cytokine during an inflammation response, the composition comprising at least one nucleic acid molecule selected from the group consisting of SEQ ID NOS 1–3.

7. The composition of claim 6, wherein the at least one cytokine is selected from the group consisting of interleukin-1, and tumor necrosis factor-α.

8. The composition of claim 7, wherein the at least one nucleic acid molecule consists of SEQ ID NO 1.

9. The composition of claim 7, wherein the at least one nucleic acid molecule consists of SEQ ID NO2.

10. The composition of claim 7, wherein the at least one nucleic acid molecule consists of SEQ ID NO: 3.

11. The composition of claim 6, wherein the inflammation response is induced by bacterial lipopolysaccharide.

12. A composition for inhibiting a MAPKAP kinase 2 dependent inflammatory response, the compositon comprising,
   at least one nucleic acid molecule selected from the group consisting of SEQ ID NOS 1–3.

\* \* \* \* \*

SEQUENCE LISTING

<160> NUMBER OF SEQ ID NOS: 3

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: designed
      antisense oligonucleotide that inhibits the expression of MAPKAP
      kinase

<400> SEQUENCE: 1
ggagttggac agcatggtgc ccggggacgc cgggg                                  35

<210> SEQ ID NO 2
<211> LENGTH: 35
<212> TYPE: DNA
<213> ORGANISM: Artificial Sequence
<220> FEATURE:
<223> OTHER INFORMATION: Description of Artifical Sequence: designed
      antisense oligonucleotide that inhibits the expression of MAPKAP
      kinase

<400> SEQUENCE: 2
cacaggcggg ggtgcccgcg gccgccccct cctcc                                  35

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: designed
      anitisense oligonucleotide that inhibits the expression of MAPKAP
      kinase

<400> SEQUENCE: 3
ggggcgggga acggcaccgg cgggctctgg ccctg                                  35